(12) United States Patent
Jung et al.

(10) Patent No.: US 12,102,421 B2
(45) Date of Patent: Oct. 1, 2024

(54) APPARATUS AND METHOD FOR MEASURING IMPEDANCE AND APPARATUS FOR ANALYZING BODY COMPOSITION

(71) Applicant: SAMSUNG ELECTRONICS CO., LTD., Suwon-si (KR)

(72) Inventors: Myoung Hoon Jung, Bucheon-si (KR); Moon Seong Park, Suwon-si (KR); Yun S Park, Suwon-si (KR); Kun Sun Eom, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 485 days.

(21) Appl. No.: 17/135,372

(22) Filed: Dec. 28, 2020

(65) Prior Publication Data

US 2021/0369135 A1   Dec. 2, 2021

(30) Foreign Application Priority Data

Jun. 2, 2020   (KR) .......................... 10-2020-0066330

(51) Int. Cl.
*A61B 5/0537*   (2021.01)
*A61B 5/273*   (2021.01)

(52) U.S. Cl.
CPC ............ *A61B 5/0537* (2013.01); *A61B 5/273* (2021.01)

(58) Field of Classification Search
CPC . A61B 5/0531; A61B 2562/04; A61B 5/0537; A61B 5/25; A61B 5/304; A61B 2562/046; A61B 5/273; A61B 5/14532; A61B 5/4869; G06F 3/0446

USPC .......................................................... 600/547
See application file for complete search history.

(56) References Cited

U.S. PATENT DOCUMENTS

| | | | |
|---|---|---|---|
| 4,674,518 A * | 6/1987 | Salo ........................ | G01F 17/00 600/526 |
| 7,738,939 B2 | 6/2010 | Hallin | |
| 8,644,919 B2 * | 2/2014 | Zdeblick ............ | A61N 1/36185 600/547 |
| 9,179,856 B2 | 11/2015 | Caduff et al. | |
| 9,962,105 B2 | 5/2018 | Choi et al. | |
| 11,284,809 B1 * | 3/2022 | Davis ................. | A61B 5/02108 |
| 2005/0192488 A1 * | 9/2005 | Bryenton ............. | A61B 5/1455 600/301 |

(Continued)

FOREIGN PATENT DOCUMENTS

| | | | | | |
|---|---|---|---|---|---|
| EP | 3586724 A1 | * | 1/2020 | ........... | A61B 5/0531 |
| WO | WO-2010085969 A1 | * | 8/2010 | ........... | A61B 5/0531 |

(Continued)

*Primary Examiner* — Yi-Shan Yang
*Assistant Examiner* — Jonathan E. Cooper
(74) *Attorney, Agent, or Firm* — Sughrue Mion, PLLC

(57) ABSTRACT

An apparatus for measuring impedance is provided. The apparatus may include an electrode part in which a plurality of electrodes are arranged; a depth controller configured to configure electrode clusters from among the plurality of electrodes of the electrode part based on a measurement depth of the object, and generate a control signal; a switch configured to connect electrodes in the electrode clusters to signal lines based on the control signal; and a measurer configured to measure the impedance of the object based on signals measured through the electrode clusters.

19 Claims, 11 Drawing Sheets

(56) References Cited

U.S. PATENT DOCUMENTS

| | | | |
|---|---|---|---|
| 2012/0245436 A1* | 9/2012 | Rutkove | A61B 5/053 |
| | | | 600/301 |
| 2014/0026678 A1* | 1/2014 | Cannard | D04B 21/14 |
| | | | 73/862.391 |
| 2018/0185651 A1* | 7/2018 | Astrom | A61N 1/36185 |
| 2019/0290152 A1* | 9/2019 | Bronstein | A61B 5/0042 |
| 2020/0146581 A1* | 5/2020 | Rhodes | G01R 31/2829 |

FOREIGN PATENT DOCUMENTS

| | | | |
|---|---|---|---|
| WO | WO-2010118538 A1 * | 10/2010 | A61B 5/0507 |
| WO | WO-2013090798 A1 * | 6/2013 | A61B 5/04 |
| WO | WO-2020094357 A1 * | 5/2020 | A61B 5/0531 |

* cited by examiner

APPARATUS AND METHOD FOR MEASURING IMPEDANCE AND APPARATUS FOR ANALYZING BODY COMPOSITION

CROSS-REFERENCE TO RELATED APPLICATION(S)

This application is based on and claims priority under 35 U.S.C. § 119 to Korean Patent Application No. 10-2020-0066330, filed on Jun. 2, 2020, in the Korean Intellectual Property Office, the disclosure of which is incorporated by reference herein in its entirety.

BACKGROUND

1. Field

The disclosure relates to an apparatus and method for measuring bioimpedance, and an apparatus for analyzing body composition using the bioimpedance.

2. Description of Related Art

A variety of medical devices are being developed to diagnose a patient's health condition. Due to the convenience of the patient, the rapidity of the medical examination result, and the like, in the medical examination process, the importance of the medical devices for measuring a bioelectric signal of the patient is emphasized. In particular, bioimpedance may be used to monitor the health or emotional state of a living body, and recently, various studies have been conducted to manufacture a device for measuring bioimpedance in a smaller size while still providing a method of measuring the bioimpedance quickly and accurately.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Additional aspects will be set forth in part in the description which follows and, in part, will be apparent from the description, or may be learned by practice of the presented embodiments.

According to an aspect of an example embodiment, an apparatus for measuring impedance of an object may include an electrode part in which a plurality of electrodes are arranged; a depth controller configured to configure electrode clusters from among the plurality of electrodes of the electrode part based on a measurement depth of the object, and generate a control signal; a switch configured to connect electrodes in the electrode clusters to signal lines based on the control signal; and a measurer configured to measure the impedance of the object based on signals measured through the electrode clusters.

The one or more measurement depths of the object may be preset based on at least one from among a type of body composition to be analyzed, a measurement site, and user characteristic information.

The depth controller may be configured to determine a width of the electrode clusters and a gap between the electrode clusters based on the measurement depth of the object, and generate the control signal based on the width of the electrode clusters and the gap between the electrode clusters.

The depth controller may be configured to determine the width of the electrode clusters and the gap between the electrode clusters based on a predefined electrode arrangement structure.

The predefined electrode arrangement structure may be a Wenner electrode array or a Wenner-Schlumberger electrode array.

The depth controller may be configured to determine a number of electrode clusters to be configured based on a predefined electrode mode.

The electrode clusters may include at least one current electrode cluster and at least one voltage electrode cluster.

The measurer may be configured to measure the impedance of the object by applying a current to the current electrode cluster and using a voltage applied to the voltage electrode cluster.

The measurer may be configured to measure the impedance of the object by applying a constant voltage to the voltage electrode cluster and measuring a current flowing in the current electrode cluster.

The plurality of electrodes of the electrode part may be arranged in a one-dimensional array, a multi-dimensional array, or a strip electrode structure.

According to an aspect of an example embodiment, a method of measuring impedance of an object may include configuring electrode clusters based on a measurement depth of the object; generating a control signal based on configuring the electrode clusters; connecting electrodes in the electrode clusters, from among a plurality of electrodes, to signal lines based on the control signal; and measuring impedance of the object using the electrode clusters.

The method may include determining a width of the electrode clusters and a gap between the electrode clusters based on the measurement depth of the object; and generating the control signal based on determining the width of the electrode clusters and the gap between the electrode clusters.

The method may include determining the width of the electrode clusters and the gap between the electrode clusters based on a predefined electrode arrangement structure; and generating the control signal based on determining the width of the electrode clusters and the gap between the electrode clusters.

The method may include determining a number of the electrode clusters based on a predefined electrode mode; and generating the control signal based on determining the number of the electrode clusters.

The electrode clusters may include at least one current electrode cluster and at least one voltage electrode cluster.

The measuring of the impedance may include measuring the impedance of the object by applying a current to the current electrode cluster and using a voltage applied to the voltage electrode cluster.

The measuring of the impedance may include measuring the impedance of the object by applying a constant voltage to the voltage electrode cluster and measuring a current flowing in the current electrode cluster.

According to an aspect of an example embodiment, an apparatus for analyzing a body composition of an object may include an impedance measurement sensor configured to configure electrode clusters from among a plurality of electrodes based on a measurement depth of the object, connect the electrodes of the configured electrode clusters to signal lines, and measure impedance of the object using the configured electrode clusters; and a processor configured to analyze the body composition of the object based on the measured impedance.

The processor may be further configured to select one or more measurement depths of the object based on a request for analyzing the body composition, and control the impedance measurement sensor based on the one or more selected measurement depths.

The body composition may include at least one from among body fat percentage, body water, blood sugar, cholesterol, triglyceride, protein, and uric acid.

Other features and aspects will be apparent from the following detailed description, the drawings, and the claims.

BRIEF DESCRIPTION OF THE DRAWINGS

The above and other aspects, features, and advantages of certain embodiments of the present disclosure will be more apparent from the following description taken in conjunction with the accompanying drawings, in which.

Figure 1:
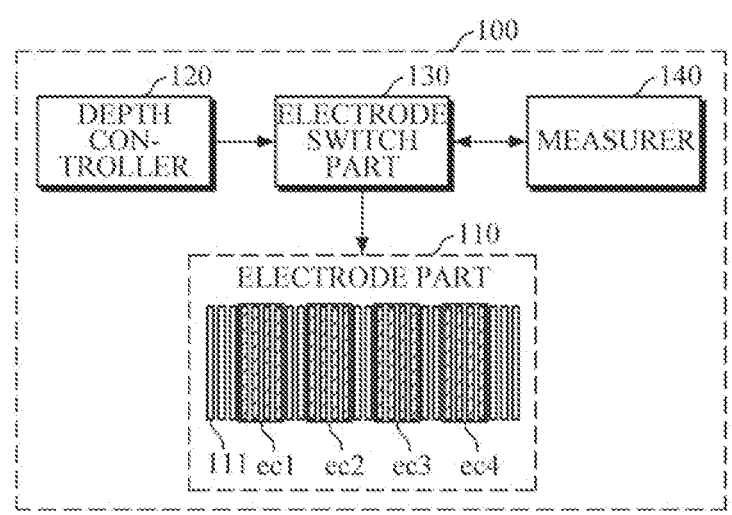
FIG. 1 is a block diagram illustrating an apparatus for measuring impedance according to an embodiment.

Throughout the drawings and the detailed description, unless otherwise described, the same drawing reference numerals will be understood to refer to the same elements, features, and structures. The relative size and depiction of these elements, features, and structures may be exaggerated for clarity, illustration, and convenience.

DETAILED DESCRIPTION

Details of example embodiments are provided in the following detailed description with reference to the accompanying drawings. The disclosure may be understood more readily by reference to the following detailed description of example embodiments and the accompanying drawings. The disclosure may, however, be embodied in many different forms and should not be construed as being limited to the embodiments set forth herein. Rather, these embodiments are provided so that the disclosure will be thorough and complete and will fully convey the concept of the disclosure to those skilled in the art, and the disclosure will only be defined by the appended claims. Like reference numerals refer to like elements throughout the specification.

It will be understood that, although the terms "first," "second," etc. may be used herein to describe various elements, these elements should not be limited by these terms. These terms are only used to distinguish one element from another. Also, the singular forms of terms are intended to include the plural forms of the terms as well, unless the context clearly indicates otherwise. In the specification, unless explicitly described to the contrary, the word "comprise," and variations such as "comprises" or "comprising," will be understood to imply the inclusion of stated elements but not the exclusion of any other elements. Terms such as "unit" and "module" denote units that process at least one function or operation, and the units may be implemented by using hardware, software, or a combination of hardware and software.

FIG. 1 is a block diagram illustrating an apparatus for measuring impedance according to an embodiment.

Referring to FIG. 1, an apparatus 100 for measuring impedance may include an electrode part 110, a depth controller 120, an electrode switch part 130, and a measurer 140.

The electrode part 110 may include a plurality of electrodes 111 arranged to be in contact with an object. In this case, each of the electrodes 111 may be configured to have a relatively smaller size compared to a standard electrode size. The electrode part 110 may be formed to have a one-dimensional array structure of the plurality of electrodes 111, or to have a multi-dimensional array structure with a plurality of one-dimensional arrays. However, the embodiment is not limited thereto, and the electrode part 110 may be formed to have a strip electrode structure by pixelating all the electrodes 111. As described above, since the electrode part 110 is formed to have an electrode structure in various forms, it is possible to detect depth information using various electrode combinations in various directions.

The depth controller 120 may select at least some of the electrodes of the electrode part 110 according to a measurement depth of the object, configure electrode clusters in units of a predetermined number of electrodes, and generate control signals according to the formed electrode clusters. In this case, the object may be a body part of the user, and may include, but is not particularly limited to, various parts, for example, a wrist, a finger, the back of a hand, an abdomen, a chest, a neck, an ear, and the like. One or more measurement depths of the object may be set in advance according to the type of body composition to be analyzed, a measurement site of the object, user-specific characteristic information, or the like. In this case, the user-specific characteristic information may include the user's gender, age, health condition, and the thickness of a measurement site (e.g., a thickness of a wrist), and the like.

The depth controller 120 may configure electrode clusters ec1, ec2, ec3, and ec4 to be used for measuring impedance from among the plurality of electrodes 111 of the electrode part 110 according to the measurement depth of the object. The depth controller 120 may determine the number of electrode clusters to be configured according to a predefined electrode mode. For example, when impedance is measured in a 4-electrode mode, four electrode clusters ec1, ec2, ec3, and ec4 may be configured as illustrated. However, the embodiment is not limited thereto, such that, when impedance is measured in a 2-electrode mode, two electrode clusters may be configured. In this case, the electrode mode may be preset to a specific electrode mode, or may be set dynamically each time impedance is measured. For convenience of description, an example of measuring impedance in a 4-electrode mode will be described hereinafter.

The depth controller 120 may determine a width of the electrode cluster and/or a gap between the electrode clusters according to the measurement depth of the object. In this case, the width of the electrode cluster may mean the number of electrodes to be included in each electrode cluster. Also, the gap between the electrode clusters may mean the number of electrodes existing between adjacent electrode clusters.

The depth controller 120 may select some of the plurality of electrodes 111 on the basis of the width of the electrode cluster and/or the gap between the electrode clusters determined as described above, and configure current electrode clusters (e.g., ec1 and ec4) and voltage electrode clusters (e.g., ec2 and ec3).

The depth controller 120 may select electrodes to configure electrode clusters from among the plurality of electrodes 111 by further taking into consideration a predefined electrode arrangement structure, and configure current electrode clusters (e.g., ec1 and ec4) and voltage electrode clusters (e.g., ec2 and ec3) using the selected electrodes. In this case, the predefined electrode arrangement structure may include a Wenner electrode array or a Wenner-Schlumberger electrode array.

The depth controller 120 may be connected to signal lines of the electrode switch part 130, and may transmit a control signal to the electrode switch part 130 so that the electrodes of the configured electrode cluster are connected to the signal lines. The depth controller 120 may be implemented in hardware, firmware, or a combination of hardware and software. The depth controller 120 may include a processor, a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component.

The electrode switch part 130 may electrically connect the electrodes of each electrode cluster to the signal lines on the basis of the control signal received from the depth controller 120, and maintain the electrodes to be used as a gap, that is, the electrodes that are not selected from among the plurality of electrodes 111, at a float state. In this case, the electrode switch part 130 may include a cross-point switch. The electrode switch part 130 may include a switch, a cross-point switch, a crossbar switch, a matrix switch, a rotary switch, a memory switch, a crossover switch, or the like.

The measurer 140 may be connected to the signal lines of the electrode switch part 130. The measurer 140 may measure impedance of the object using the configured electrode clusters. For example, the measurer 140 may measure impedance by applying or extracting current to or from the current electrode clusters, and measuring a voltage applied to each voltage electrode cluster. Alternatively, the measurer 140 may measure the impedance by applying a constant voltage to the voltage electrode cluster, and measuring the current flowing in the current electrode cluster. The measurer 140 may include a current source for applying an alternating electrical current, and a voltmeter for measuring a voltage. The measurer 140 may include an impedance measurement analyzer, an LCR meter, or the like.

The measurer 140 may measure impedance at various depths as the depth controller 120 configures various electrode clusters while adjusting the measurement depth. In addition, the measurer 140 may measure a plurality of impedances while changing a frequency of an input current within a predetermined band of frequencies (e.g., 1 kHz to several hundreds of MHz).

Figure 2A:
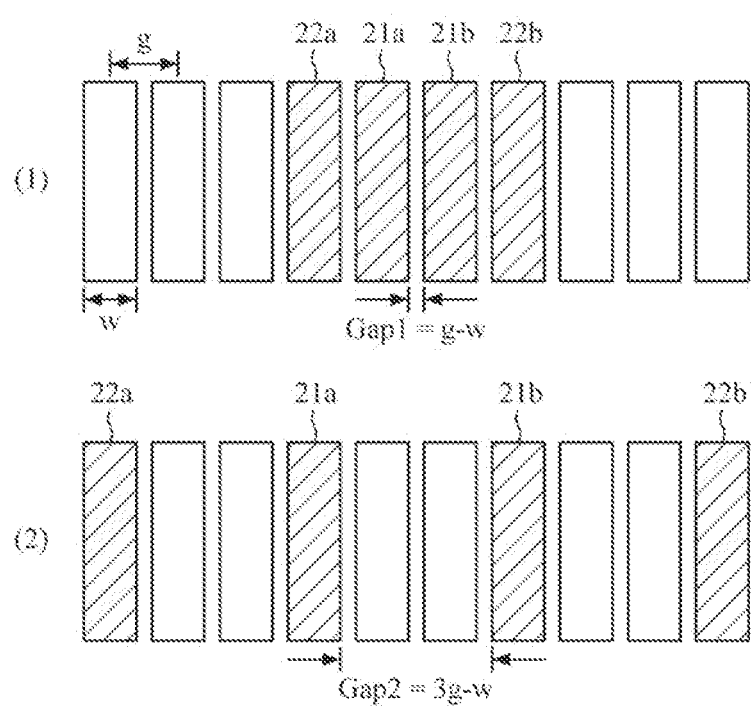
FIGS. 2A and 2B are diagrams for describing a general electrode structure.
Figure 2B:
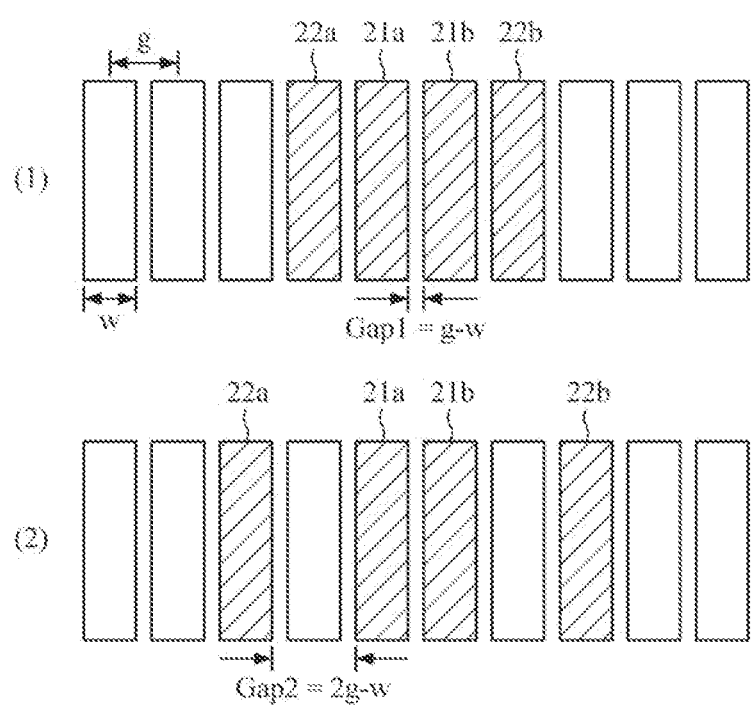

FIGS. 2A and 2B are diagrams for describing a general electrode structure. FIGS. 3A to 3D are diagrams for describing an electrode structure according to an embodiment. The electrode cluster configuration according to an embodiment will be described with reference to FIGS. 1 to 3D.

According to the present embodiment, it is possible to measure impedance for each skin layer by applying an electrical resistivity method to the measurement of bio-impedance of human skin. Generally, the electrical resistivity method may include the Wenner measurement method and a Wenner-Schlumberger measurement method. When the electrical resistivity method is applied to the surface of the ground, it is possible to freely change the measurement depth by freely changing a distance between probes, but when applied to the human body, the measurement depth is limited because electrodes with fixed spacing are used.

FIG. 2A is a diagram for describing a general Wenner electrode array. The Wenner electrode array refers to a configuration in which gaps between two voltage electrodes 21a and 21b in the middle and two outer current electrodes 22a and 22b are set to be equal to each other. In the Wenner electrode array, the measurement depth may be increased by increasing a gap between the electrodes. For example, as shown in (1) of FIG. 2A, in a case where a first depth is measured, when a distance between electrodes is g and an electrode width is w, the gap Gap1 between the electrodes is g-w. As another example, as shown in (2) of FIG. 2A, in a case where a second depth is measured, a gap Gap2 between the electrodes is 3g-w. Therefore, the gap between the electrodes is increased by units of 2g in order to increase the measurement depth from the first depth to the second depth. The electrode width w cannot be greater than the distance g between the electrodes, and thus the smallest unit by which the gap between the electrodes increase, that is, depth resolution ($\Delta Gap=Gap2-Gap1=2g$), cannot be smaller than 2w. Therefore, the measurement depth is about w because the measurement depth becomes about half of the gap between the electrodes.

FIG. 2B is a diagram for describing a general Wenner-Schlumberger electrode array. The Wenner-Schlumberger electrode array refers to a configuration in which a gap between two voltage electrodes 21a and 21b in the middle is maintained constant, and gaps between each of outer two current electrodes 22a and 22b and a voltage electrode adjacent thereto are increased. For example, as shown in (1) of FIG. 2B, in a case where a first depth is measured, when a distance between electrodes is g and an electrode width is w, the gap Gap1 between the electrodes is g-w. As another example, as shown in (2) of FIG. 2B, when a second depth is measured, the gap Gap2 between the electrodes is 2g-w. Therefore, the smallest unit (i.e., depth resolution=$\Delta Gap=Gap2-Gap1=g$) by which the gap between the electrodes increases cannot be smaller than w.

As described above, in the Wenner electrode array and the Wenner-Schlumberger electrode array, the depth resolution is generally limited by the electrode width w. However, according to the present embodiment, the voltage electrodes and the current electrodes are replaced with electrode clusters, each of which is an aggregate of a plurality of electrodes, thereby permitting the gap between the electrodes to be finely adjusted while increasing the total electrode area. Accordingly, a high signal-to-noise ratio (SNR) may be obtained by reducing contact resistance, and it is possible to increase a resolution for each depth.

Figure 3A:
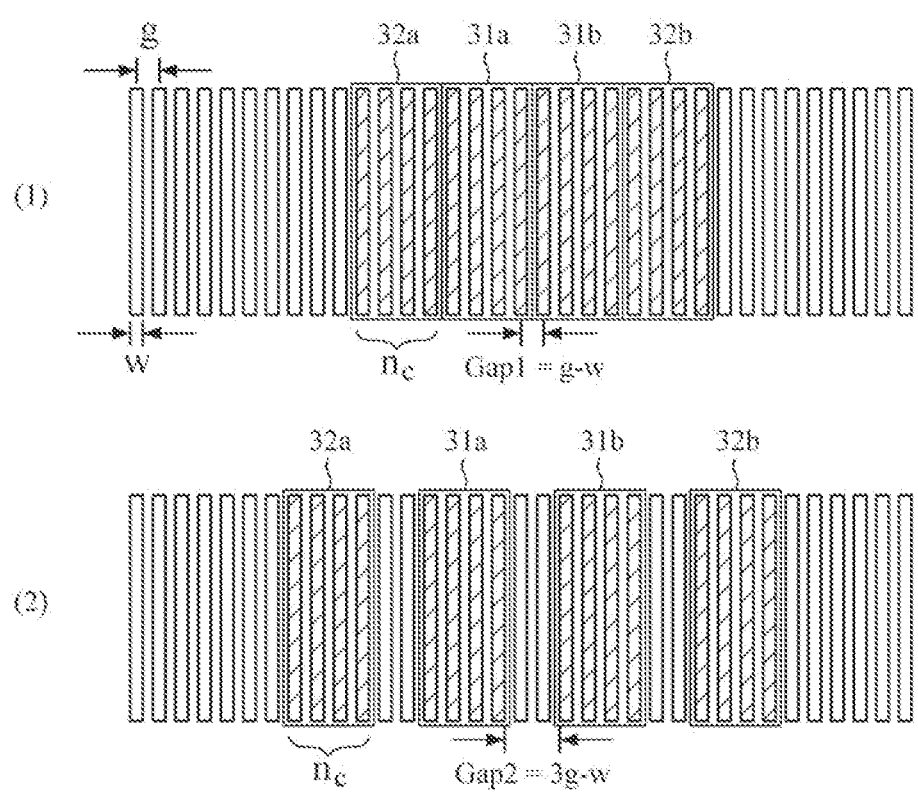
FIGS. 3A to 3D are diagrams for describing an electrode structure according to an embodiment.

FIG. 3A is a diagram for describing a Wenner electrode array according to an embodiment. In a cluster electrode-based Wenner electrode array, an effective electrode width $g_{eff}$ is the sum ($g \times nc$) of widths of small electrodes of each of electrode clusters 31a, 31b, 32a, and 32b. Here, nc may denote the number of small electrodes included in each of the electrode clusters 31a, 31b, 32a, and 32b. In addition, since a gap between the electrodes changes in units of the small electrodes, it is possible to increase a depth resolution while keeping the electrode width wide. Therefore, as shown in (1) of FIG. 3A, when a first depth is measured, the gap Gap1 between the electrodes is g-w, and as shown in (2) of FIG. 3A, when a second depth is measured, the gap Gap2 between the electrodes is 3g-w, and hence the effective electrode width may be maintained at g×nc while changing the gap between the electrodes by 2g.

Figure 3B:
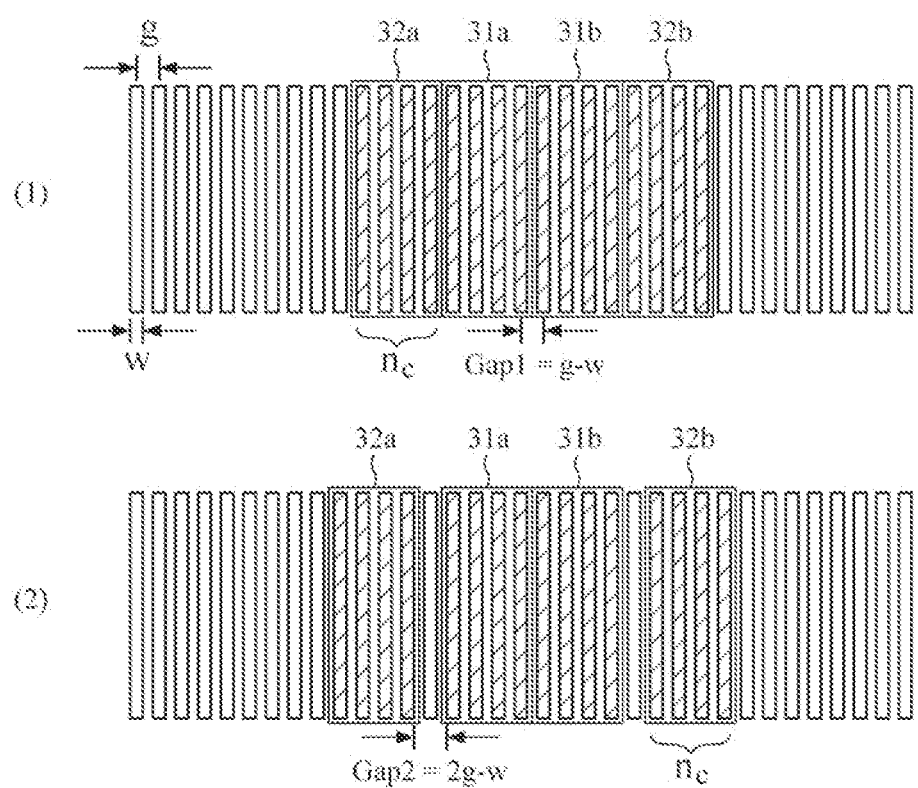

FIG. 3B is a diagram for describing a Wenner-Schlumberger electrode array according to an embodiment. As shown in (1) of FIG. 3B, when a first depth is measured, the gap Gap1 between electrodes is g-w, and as shown in (2) of FIG. 3B, when a second depth is measured, the gap Gap2 between the electrodes is 2g-w, and hence the effective electrode width may be maintained at g×nc while changing the gap between the electrodes by g. Therefore, according to the present embodiment, it is possible to freely change the gap between the electrodes irrespective of the electrode area.

Figure 3C:
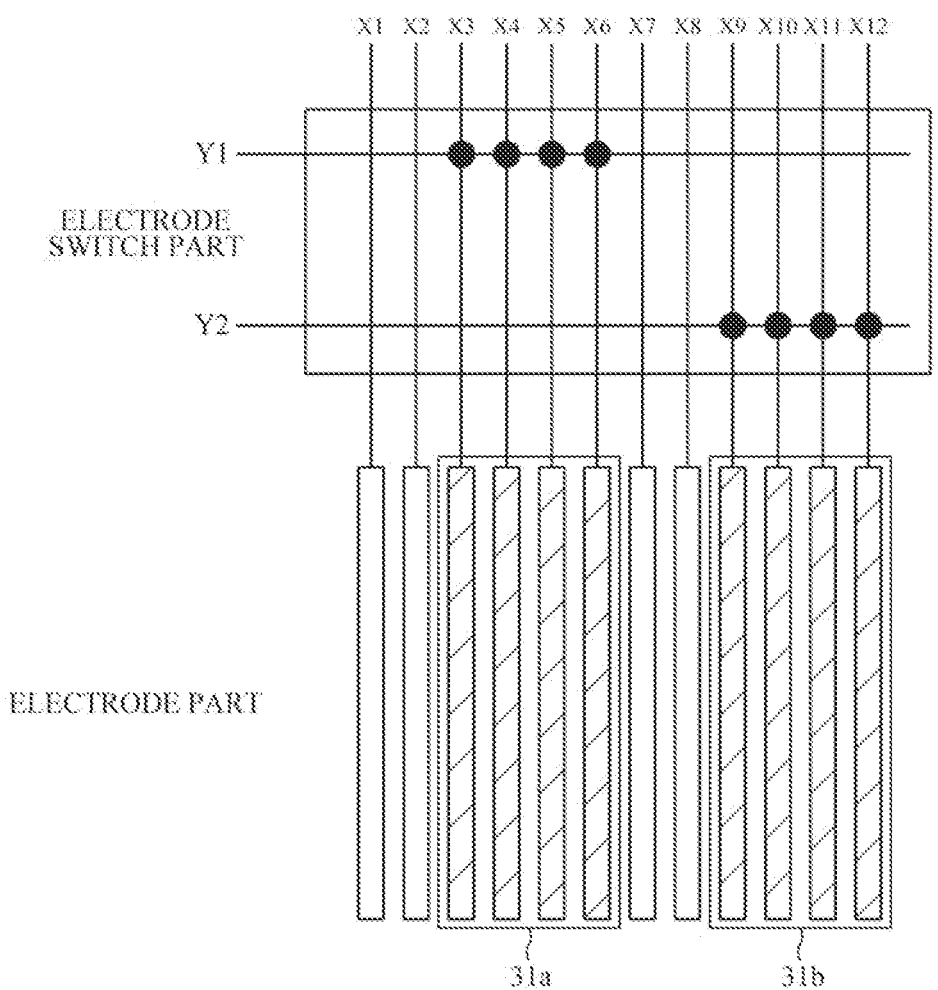

Referring to FIG. 3C, the electrode switch part 130 may be configured as a cross-point switch capable of multi-to-multi input/output. Two electrode clusters 31a and 31b are illustrated for convenience of description, but various numbers of electrode clusters may be configured according to the electrode mode. X-axis signal lines X1 to X12 may be connected to the respective electrodes of the electrode part 110 and the depth controller 120. In addition, Y-axis signal lines Y1 and Y2 may be connected to the measurer 140.

When the depth controller 120 configures electrode clusters 31a and 31b and generates a control signal, the electrode switch part 130 may turn on switches of the X-axis signal lines X3 to X6 connected to electrodes of a first electrode cluster 31a, thereby connecting to the Y-axis signal line Y1, and may turn on switches of the X-axis signal lines X9 to X12 connected to electrodes of a second electrode cluster 31b, thereby connecting to the Y-axis signal line Y2. Also, the remaining X-axis signal lines X1, X2, X7, and X8 may be switched off to cut off the connection to the Y-axis signal lines Y1 and Y2. The measurer 140 may receive current application and a voltage signal through the Y-axis signal lines Y1 and Y2.

Figure 3D:
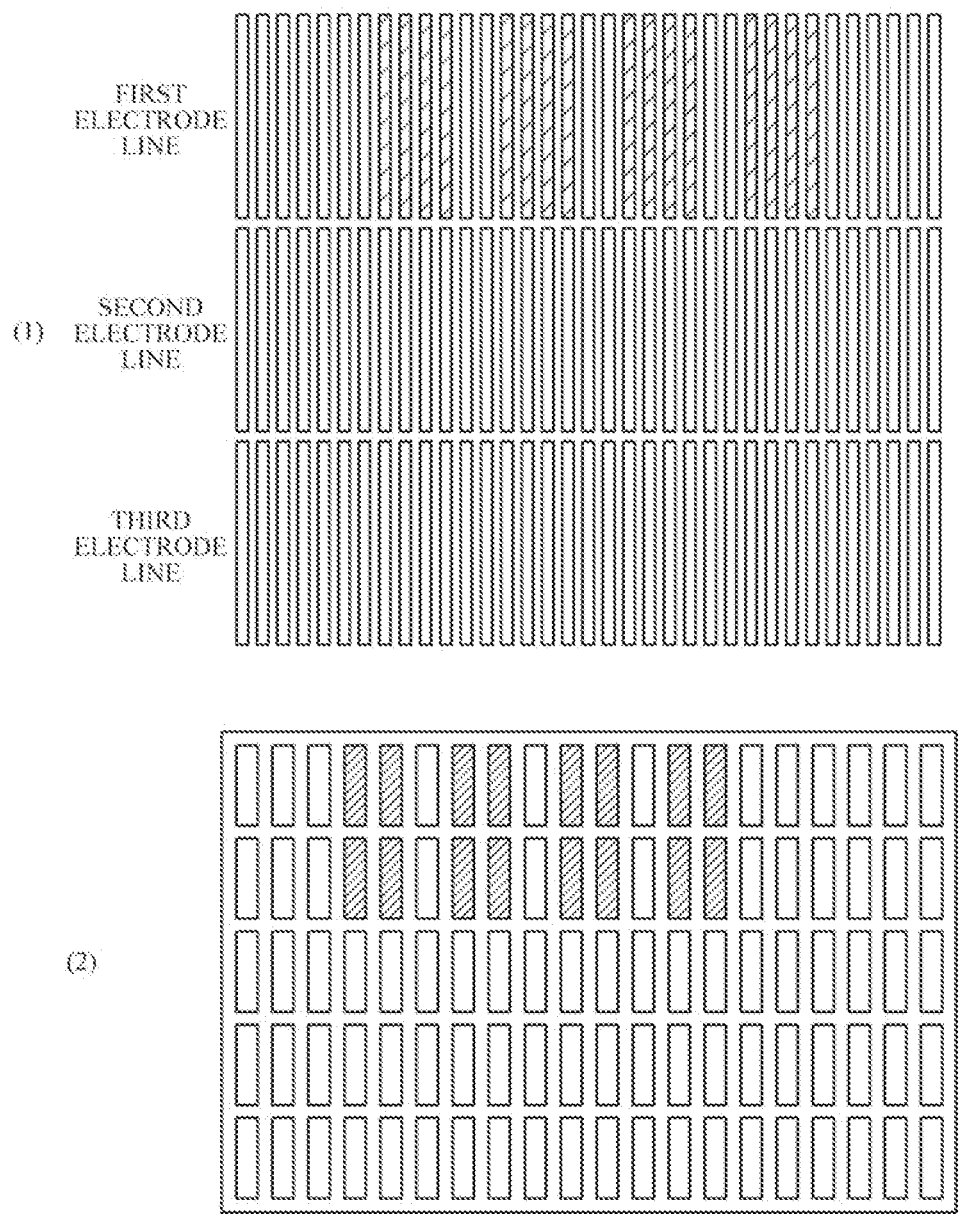

FIG. 3D is a diagram illustrating an example of an electrode arrangement structure of an electrode part 110 according to an embodiment. As described above, the plurality of electrodes 111 of the electrode part 110 may be configured in a one-dimensional array (e.g., a case where only a first electrode line is configured as shown in (1) of FIG. 3D). Alternatively, as shown in (1) of FIG. 3D, the electrode part 110 may be configured in a multi-dimensional array in which a plurality of one-dimensional electrode lines (a first electrode, a second electrode line, and a third electrode line) are arranged. Alternatively, as shown in (2) of FIG. 3D, the electrode part 110 may be configured to have a strip electrode structure by pixelating the plurality of electrodes. As described above, since the electrode part 110 is configured to have an electrode arrangement structure in various forms, it is possible to detect a plurality of depth information using various electrode combinations in various directions.

Figure 4:
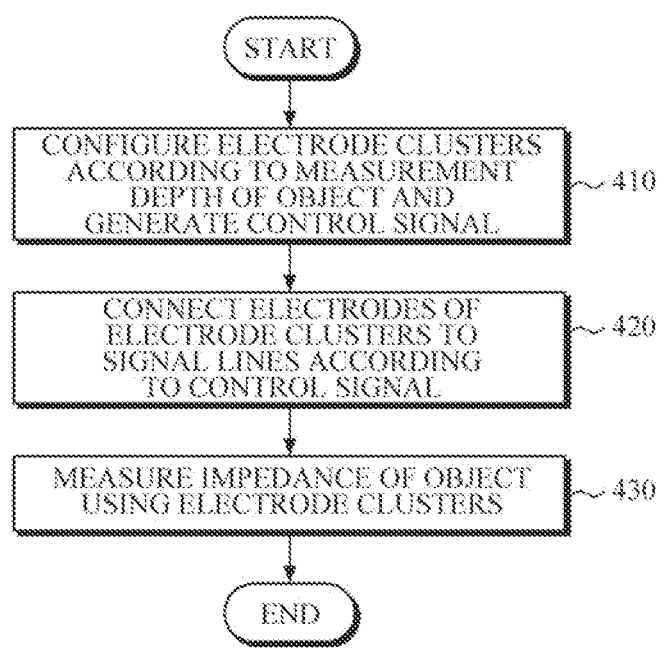
FIG. 4 is a flowchart illustrating a method of measuring impedance according to an embodiment.

FIG. 4 is a flowchart illustrating a method of measuring impedance according to an embodiment. The method of FIG. 4 is an embodiment of a method of estimating bio-information performed by the apparatus 100 of FIG. 1 for measuring impedance. The method has been described in detail above, and hence will be briefly discussed hereinafter.

First, the apparatus 100 for measuring impedance may configure electrode clusters according to a measurement depth of an object and generate a control signal (operation 410). One or more measurement depths of the object may be set on the basis of the type of body composition to be analyzed, a measurement site of the object, user-specific characteristic information, or the like. The number of electrode clusters, the width of the electrode clusters, and/or the gap between the electrode clusters may be determined according to the measurement depth of the object, the electrode mode, the electrode arrangement structure, and the like, and some electrodes may be selected from among the plurality of electrodes according to the determination result to configure the electrode clusters.

Then, the electrodes in the electrode clusters may be connected to signal lines according to a control signal (operation 420). The apparatus 100 for measuring impedance may connect the electrodes in the electrode clusters to the signal lines using, for example, one or more cross-point switches, and may switch off electrodes other than those included in the electrode clusters, that is, electrodes used as the gap, to maintain the electrodes at a float state.

Then, the impedance of the object may be measured using the electrode clusters (operation 430). For example, the apparatus 100 for measuring impedance may measure the impedance by applying a current to the current electrode cluster and measuring a voltage applied to the voltage electrode cluster. Alternatively, the apparatus 100 may measure the impedance by applying a constant voltage to the voltage electrode cluster and measuring a current from the current electrode cluster.

Figure 5:
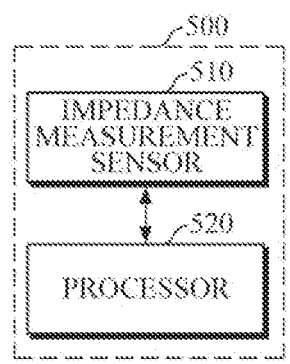
FIG. 5 is a block diagram of an apparatus for analyzing body composition according to an embodiment.

FIG. 5 is a block diagram of an apparatus for analyzing body composition according to an embodiment.

Examples of an apparatus 500 for analyzing body composition may be mounted in a device of a professional medical institution, a wearable device (e.g., a smartwatch worn on a wrist, a smart band type wearable device, a headphone type wearable device, a hair band type wearable device, or the like), a mobile device (e.g., a smartphone, a tablet PC, or the like), or the like.

Referring to FIG. 5, the apparatus 500 for analyzing body composition includes an impedance measurement sensor 510 and a processor 520. The impedance measurement sensor 510 and the processor 520 may be integrally formed in one piece of hardware. Alternatively, the impedance measurement sensor 510 and the processor 520 may be separately formed as individual pieces of hardware, and may be connected electrically or by a wired or wireless communication connection.

The impedance measurement sensor 510 may correspond to the apparatus 100 which has been described in detail above in connection with FIG. 1 as an embodiment for measuring impedance and will be briefly described below.

The impedance measurement sensor 510 may include an electrode part in which a plurality of electrodes are arranged in various forms, such as a one-dimensional array, a multi-dimensional array, or a strip electrode structure, and a depth controller configured to configure an electrode cluster according to a measurement depth of an object. Also, an electrode switch part may be included to connect the electrodes in the electrode cluster to signal lines according to a control signal of the depth controller and to separate electrodes other than those included in the electrode cluster from the signal lines. Moreover, the impedance measurement sensor 510 may include a measurer configured to measure impedance from the object using the configured electrode cluster and to transmit the measured impedance to the processor 520.

The processor 520 may be connected to the impedance measurement sensor 510, and may control the impedance measurement sensor 510 according to a request for analyzing body composition. The request for analyzing body composition may occur according to a user's input or at an interval predetermined in the apparatus 500. In this case, the body composition may include, but is not limited to, body fat percentage, body water, blood sugar, cholesterol, triglyceride, protein, uric acid, and the like.

When the request for analyzing body composition is received, the processor 520 may select one or more measurement depths from among a plurality of predefined measurement depths according to the type of body composition, the measurement site of the user, user's characteristic information, or the like. In this case, the plurality of measurement depths may be obtained through a preprocessing process performed on a plurality of users for each type of body composition. In addition, the depth of blood vessels may be different for measurement sites, such as a wrist, the back of a hand, an abdomen, an ear, a neck, the back of a foot, or the like, the measurement depth may be set for each measurement site. Additionally, the measurement depth personalized for each user through preprocessing may be obtained to reflect the user's characteristics, such as the user's age, gender, and health condition, the thickness of the measurement site of an object, and the like. The user's personalized measurement depth may be obtained again according to a calibration interval or a user's request.

The processor 520 may transmit the measurement depth information to the depth controller of the impedance measurement sensor 510. When the processor 520 is configured to obtain impedance from a plurality of measurement depths for analyzing body composition, the processor 520 may transmit first measurement depth information to the depth controller of the impedance measurement sensor 510, and when receiving impedance information regarding the first measurement depth from the measurer of the impedance measurement sensor 510, the processor 520 may transmit second measurement depth information to the depth controller. In this way, a plurality of impedances may be obtained while changing the measurement depth.

The processor 520 may receive an impedance value from the measurer of the impedance measurement sensor 510, and analyze body composition on the basis of the received impedance value. For example, the processor 520 may acquire the body composition value using an analysis model that defines a correlation between the impedance value and the body composition as a linear or nonlinear relational expression. In this case, the analysis model may be configured through various methods, such as a linear function equation, a linear/nonlinear regression analysis, a neural network, deep learning, and the like. However, the embodiment is not limited thereto, such that the processor 520 may model the measured impedance as a predefined equivalent circuit to extract a parameter related to a physical characteristic of the body composition, and estimate the body composition using an analysis model that defines a correlation between the extracted parameter and the body composition.

The processor 520 may be implemented in hardware, firmware, or a combination of hardware and software. The processor 520 may include a CPU, a GPU, an APU, a microprocessor, a microcontroller, a DSP, an FPGA, an ASIC, or another type of processing component.

Figure 6:
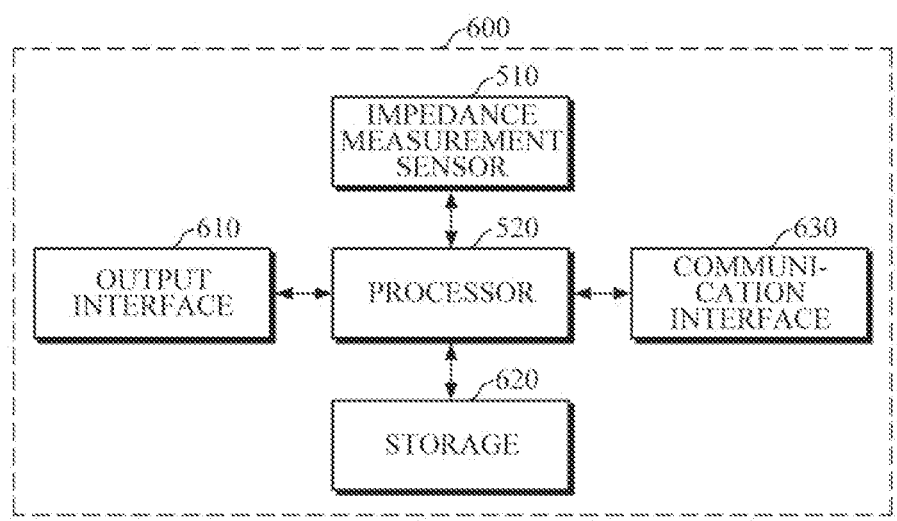
FIG. 6 is a block diagram illustrating an apparatus for analyzing body composition according to another embodiment.

FIG. 6 is a block diagram illustrating an apparatus for analyzing body composition according to another embodiment.

Referring to FIG. 6, an apparatus 600 for analyzing body composition may include an impedance measurement sensor 510, a processor 520, an output interface 610, a storage 620, and a communication interface 630. The impedance measurement sensor 510 and the processor 520 have been described in detail above and hence descriptions thereof will be omitted below.

The output interface 610 may provide a user with a processing result of the processor 520. For example, the output interface 610 may visually provide the processing result to the user using a display. The output interface 610 may divide the display into two or more regions to output impedance information, and the like, used for an analysis to a first region and output an analysis result to a second region. In addition, analysis history data for a predetermined period may be output to the second region in a graph form, and when a user selects an analysis result at a certain point in the graph, the information used for analyzing body composition at the selected point may be output to the first region. In this case, when an estimate value of the body composition is not within a normal range, the color or the thickness of line representing the estimate value may be adjusted so that the user can easily recognize the estimate value, or warning information may be provided to the user by displaying the normal range along with the estimate value. In another example, the output interface 610 may provide the user with the result of analyzing body composition through a non-visual method such as voice, vibration, or tactile sensation, alone or in combination with a visual display, using an voice output module, such as a speaker, or a haptic module.

The storage 620 may store a variety of reference information for analyzing body composition, the impedance measurement result, and the result of analyzing body composition. In this case, the reference information may include user characteristic information, such as the user's age, gender, health condition, and the like. In addition, the reference information may include, but not limited to, a calibration interval, calibration determination criteria, an analysis model, and the like.

The storage 620 may include at least one type of storage medium of a flash memory type, a hard disk type, a multimedia card micro type, a card type memory (for example, secure digital (SD) or extreme digital (XD) memory), a random access memory (RAM), a static random access memory (SRAM), a read-only memory (ROM), an electrically erasable programmable read-only memory (EEPROM), a programmable read-only memory (PROM), a magnetic memory, a magnetic disk, and an optical disk, but is not limited thereto.

The communication interface 640 may communicate with an external device to transmit and receive various data related to body composition analysis. The external device may include an information processing device, such as a smartphone, a tablet PC, a desktop PC, a notebook PC, and the like.

The communication interface 630 may communicate with the external device using various wired or wireless communication technologies such as Bluetooth communication, Bluetooth low energy (BLE) communication, near field communication (NFC), wireless local access network (WLAN) communication, ZigBee communication, infrared data association (IrDA) communication, wireless fidelity (Wi-Fi) direct (WFD) communication, ultra wideband (UWB) communication, Ant+ communication, Wi-Fi communication, and 3G, 4G, and 5G communication technologies. However, the communication technologies are not limited thereto.

Figure 7:
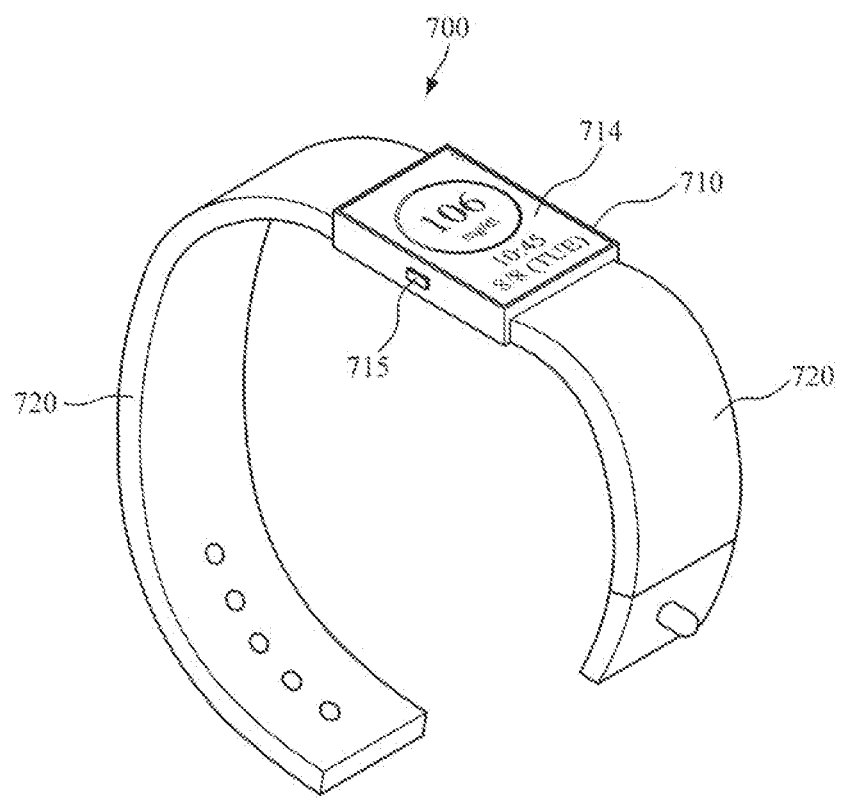
FIG. 7 is a diagram illustrating a wearable device according to an embodiment.

FIG. 7 is a diagram illustrating a wearable device according to an embodiment. FIG. 7 illustrates a wearable device, such as a smartwatch worn on a wrist of a user, or a smart band. The wearable device 700 may include various embodiments of the apparatuses 500 and 600 for analyzing body composition.

Referring to FIG. 7, the wearable device 700 includes a main body 710 and a strap 720. Various components of the apparatuses 100, 500, and 600 for analyzing body composition may be mounted in the main body 710.

The main body 719 may be worn on a wrist of a user by the strap 720. The main body 710 may include various modules for performing various functions of the wearable device 700. A battery may be embedded in the main body 710 or the strap 720 to supply power to the various modules. The strap 720 may be connected to the main body 710. The strap 720 may be flexible so as to be bent around the wrist of the user. The strap 720 may include a first strap and a second strap separate from the first strap. Respective ends of the first and second straps are connected to both sides of the main body MB and the first strap and the second strap may be fastened to each other using fastening means formed on the other sides thereof. In this case, the fastening means may be formed as Velcro fastening, pin fastening, or the like, but is not limited thereto. In addition, the strap may be formed as an integrated piece, such as a band.

An impedance measurement sensor may be mounted in the main body 710 to acquire impedance from a wrist region of the user. The impedance measurement sensor may include an electrode part in which a plurality of electrodes are arranged and may configure electrode clusters by selecting some of the plurality of electrodes in units of a cluster according to a measurement depth of an object. In addition, the impedance measurement sensor may measure impedance using the configured electrode clusters. In this case, the impedance measurement sensor may adjust the number of electrodes in each electrode cluster, the width of the electrode cluster, a gap between the electrode clusters, and the like, according to the measurement depth of the object, electrode mode, an electrode arrangement structure, and the like.

The main body 710 may include a camera module. The camera module may acquire an image of the object when the object is in contact with the main body 710.

A processor may be mounted inside the main body 710, be electrically connected to the various components, control the various components, and process information collected from the various components. For example, when an image of the object is received from the camera module, the processor may control an output interface to provide information identifying a contact position, a contact status, and the like, to the user. In addition, the processor may analyze the received image to determine a measurement site of the object, and may determine an optimal (or improved) measurement depth according to the determined measurement site.

The processor may analyze body composition using the impedance measurement result. The processor may control a display 714 to output the body composition analysis result to the user.

The display 714 may be mounted on the top of the main body 710, and may output various types of information under the control of the processor. In addition, the display 714 may include a touch screen capable of touch input, and may transmit a user's touch input to the processor.

A communication interface may be mounted in the main body 710 and may communicate with an external device. The communication interface may transmit the result of analyzing body composition to the external device such that the external device can perform various functions related to monitoring of the user's health condition. The external device may be an information processing device having a relatively high computing performance, such as a smartphone, a tablet PC, desktop PC, a notebook PC, and the like.

The wearable device 700 may further include a manipulator 715 mounted in the main body 710. The manipulator 715 may be manufactured in a form exposed to the outside from one side of the main body 710, and may receive a command input by the user and transmit the command to the processor. The manipulator 715 may have the function of turning on/off the wearable device.

The example embodiments can be implemented by computer-readable code stored in a non-transitory computer-readable medium, and executed by one or more processors. Code and code segments constituting the computer program can be inferred by a computer programmer skilled in the art. The non-transitory computer-readable medium includes all types of recording media in which computer-readable data is stored. Examples of the non-transitory computer-readable medium include a ROM, a RAM, a CD-ROM, a magnetic tape, a floppy disk, and an optical data storage. Further, the computer-readable medium may be implemented in the form of a carrier wave such as Internet transmission. In addition, the non-transitory computer-readable medium may be distributed to computer systems over a network, in which computer readable code may be stored and executed in a distributed manner.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An apparatus for measuring impedance of an object, the apparatus comprising:
   an electrode part in which a plurality of electrodes are arranged;
   at least one processor configured to operate as a depth controller to configure electrode clusters from among the plurality of electrodes of the electrode part based on a measurement depth of the object, and generate a control signal, wherein the electrode clusters include a first electrode cluster comprising a first electrode and a second electrode disposed side by side in the plurality of electrodes, the first electrode and second electrode being connected to a first Y-axis signal line of a cross-point switch, and a second electrode cluster comprising a third electrode and a fourth electrode disposed side by side in the plurality of electrodes, the third electrode and the fourth electrode connected to a second Y-axis signal line of the cross-point switch, wherein the first electrode cluster and the second electrode cluster are controlled together;
   the cross-point switch comprising a plurality of X-axis signal lines connected to each of the plurality of electrodes, the first Y-axis signal line and the second Y-axis signal line that intersect the X-axis signal lines, and configured to electrically connect the first electrode and the second electrode in the first electrode cluster to the first Y-axis signal line by switching on the X-axis signal lines connected to the first electrode and the second electrode in the first electrode cluster, and configured to electrically connect the third electrode and the fourth electrode in the second electrode cluster to the second Y-axis signal line by switching on the X-axis signal lines connected to the third electrode and the fourth electrode in the second electrode cluster, based on the control signal; and a meter for measuring the impedance of the object based on signals measured through the electrode clusters, wherein the depth controller is further configured to determine a width of the first and second electrode clusters and a gap between the first and second electrode clusters based on the measurement depth of the object, and generate the control signal based on the width of the electrode clusters and the gap between the electrode clusters.

2. The apparatus of claim 1, wherein one or more measurement depths of the object are preset based on at least one from among a type of body composition to be analyzed, a measurement site, and user characteristic information.

3. The apparatus of claim 1, wherein the depth controller is further configured to determine the width of the electrode clusters and the gap between the electrode clusters based on a predefined electrode arrangement structure.

4. The apparatus of claim 3, wherein the predefined electrode arrangement structure is a Wenner electrode array or a Wenner-Schlumberger electrode array.

5. The apparatus of claim 1, wherein the depth controller is further configured to determine a number of the electrode clusters to be configured based on a predefined electrode mode, wherein the electrode mode is selectively switched between two or more electrode modes, and each electrode mode includes at least two electrodes disposed side by side and controlled together.

6. The apparatus of claim 1, wherein the electrode clusters include at least one current electrode cluster and at least one voltage electrode cluster.

7. The apparatus of claim 6, wherein the meter measures the impedance of the object by applying a current to the current electrode cluster and using a voltage applied to the voltage electrode cluster.

8. The apparatus of claim 6, wherein the meter measures the impedance of the object by applying a constant voltage to the voltage electrode cluster and measuring a current flowing in the current electrode cluster.

9. The apparatus of claim 1, wherein the plurality of electrodes of the electrode part are arranged in a one-dimensional array, a multi-dimensional array, or a strip electrode structure.

10. A method of measuring impedance of an object, the method comprising:

configuring electrode clusters based on a measurement depth of the object; generating a control signal based on configuring the electrode clusters, wherein the electrode clusters include a first electrode cluster comprising a first electrode and a second electrode disposed side by side in a plurality of electrodes, the first electrode and the second electrode being connected to a first Y-axis signal line of a cross-point switch, and a second electrode cluster comprising a third electrode and a fourth electrode disposed side by side in the plurality of electrodes, the third electrode and the fourth electrode being connected to a second Y-axis signal line of a cross-point switch, wherein the first electrode cluster and the second electrode cluster are controlled together, wherein the cross-point switch comprises a plurality of X-axis signal lines connected to each of the plurality of electrodes, the first Y-axis signal line and the second Y-axis signal line that intersect the X-axis signal lines, and configured to electrically connect the first electrode and the second electrode in the first electrode cluster to the first Y-axis signal line by switching on the X-axis signal lines connected to the first electrode and the second electrode in the first electrode cluster, and configured to electrically connect the third electrode and the fourth electrode in the second electrode cluster to the second Y-axis signal line by switching on the X-axis signal lines connected to the third electrode and the fourth electrode in the second electrode cluster;

connecting electrodes in the electrode clusters, from among a plurality of electrodes, to signal lines based on the control signal; and measuring impedance of the object using the electrode clusters, determining a width of the first and second electrode clusters and a gap between the first and second electrode clusters based on a predefined electrode arrangement structure; and generating the control signal based on determining the width of the electrode clusters and the gap between the electrode clusters.

11. The method of claim 10, further comprising:

determining a number of the electrode clusters to be configured based on a predefined electrode mode; and generating the control signal based on determining the number of the electrode clusters to be configured.

12. The method of claim 10, wherein the electrode clusters include at least one current electrode cluster and at least one voltage electrode cluster.

13. The method of claim 12, wherein the measuring of the impedance comprises measuring the impedance of the object by applying a current to the current electrode cluster and using a voltage applied to the voltage electrode cluster.

14. The method of claim 12, wherein the measuring of the impedance comprises measuring the impedance of the object by applying a constant voltage to the voltage electrode cluster and measuring a current flowing in the current electrode cluster.

15. An apparatus for analyzing a body composition of an object, the apparatus comprising:

a meter configured to configure electrode clusters from among a plurality of electrodes based on a measurement depth of the object, connect the electrodes of the configured electrode clusters to signal lines, and measure impedance of the object using the configured electrode clusters, wherein the electrode clusters include a first electrode cluster comprising a first electrode and a second electrode disposed side by side in the plurality of electrodes, the first electrode and the second electrode being connected to a first Y-axis signal line of a cross-point switch, and a second electrode cluster comprising a third electrode and a fourth electrode disposed side by side in the plurality of electrodes, the third electrode and the fourth electrode being connected to a second Y-axis signal line of the cross-point switch, wherein the cross-point switch comprises a plurality of X-axis signal lines connected to each of the plurality of electrodes, the first Y-axis signal line and the second Y-axis signal line that intersect the X-axis signal lines, and configured to electrically connect the first electrode and the second electrode in the first electrode cluster to the first Y-axis signal line by switching on the X-axis signal lines connected to the first electrode and the second electrode in the first electrode cluster, and configured to electrically connect the third electrode and the fourth electrode in the second electrode cluster to the second Y-axis signal line by switching on the X-axis signal lines connected to the third electrode and the fourth electrode in the second electrode cluster, wherein the first electrode cluster and the second electrode cluster are controlled together; and a processor configured to analyze the body composition of the object based on the measured impedance, wherein the meter is further configured to determine a width of the first and second electrode clusters and a gap between the first and second electrode clusters based on the measurement depth of the object, and generate the control signal based on the width of the electrode clusters and the gap between the electrode clusters.

16. The apparatus of claim 15, wherein the processor is further configured to select one or more measurement depths of the object based on a request for analyzing the body composition, and control the meter based on the one or more selected measurement depths.

17. The apparatus of claim 15, wherein the body composition includes at least one from among body fat percentage, body water, blood sugar, cholesterol, triglyceride, protein, and uric acid.

18. The apparatus of claim 1 wherein one or more measurement depths of the object are preset based on a body part of the object, wherein the body part is selected from at least one of a wrist, finger, hand, abdomen, chest, neck and ear.

19. The apparatus of claim 1, wherein the first electrode cluster and the second electrode cluster are activated and deactivated together.

\* \* \* \* \*